US007918900B2

(12) United States Patent
Cottard et al.

(10) Patent No.: US 7,918,900 B2
(45) Date of Patent: Apr. 5, 2011

(54) PROCESS FOR THE PREDICTABLE DYEING OF KERATINOUS FIBERS COMPRISING APPLYING AT LEAST ONE COMPOSITION COMPRISING AT LEAST ONE DIAMINO-N, N-DIHYDROPYRAZOLONE DERIVATIVE AND AT LEAST ONE COMPOSITION CHOSEN FROM FUNDAMENTAL AND/OR GOLDEN-HIGHLIGHTS COMPOSITIONS

(75) Inventors: François Cottard, Courbevoie (FR); Jean-Marc Ascione, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/812,616

(22) Filed: Jun. 20, 2007

(65) Prior Publication Data
US 2008/0005853 A1 Jan. 10, 2008

Related U.S. Application Data

(60) Provisional application No. 60/816,861, filed on Jun. 28, 2006.

(30) Foreign Application Priority Data

Jun. 20, 2006 (FR) ..................................... 06 52549

(51) Int. Cl.
*A61Q 5/10* (2006.01)
*C07D 231/44* (2006.01)

(52) U.S. Cl. ............. 8/405; 8/406; 8/407; 8/408; 8/410; 8/411; 8/412; 8/421; 8/567; 132/202; 132/208; 548/369.1

(58) Field of Classification Search .............. 8/406, 407, 8/408, 410, 411, 412, 421, 567, 405; 514/406, 514/407; 548/369.1; 132/202, 208
See application file for complete search history.

(56) References Cited

U.S. PATENT DOCUMENTS

| 3,012,884 | A | 12/1961 | de Ramaix et al. |
| 4,003,699 | A | 1/1977 | Rose et al. |
| 4,128,425 | A | 12/1978 | Greenwald |
| RE30,199 | E | 1/1980 | Rose et al. |
| 4,823,985 | A | 4/1989 | Grollier et al. |
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,718,731 | A | 2/1998 | Loewe et al. |
| 5,766,576 | A | 6/1998 | Löwe et al. |
| 6,099,592 | A | 8/2000 | Vidal et al. |
| 6,099,593 | A | 8/2000 | Terranova et al. |
| 6,284,003 | B1 | 9/2001 | Rose et al. |
| 6,338,741 | B1 | 1/2002 | Vida et al. |
| 6,436,151 | B2 | 8/2002 | Cottard et al. |
| 6,645,258 | B2 | 11/2003 | Vidal et al. |
| 6,660,046 | B1 | 12/2003 | Terranova et al. |
| 6,730,789 | B1 | 5/2004 | Birault et al. |
| 7,285,137 | B2 * | 10/2007 | Vidal et al. ........................ 8/405 |
| 7,485,156 | B2 | 2/2009 | Saunier |
| 7,488,355 | B2 | 2/2009 | Saunier |
| 7,488,356 | B2 | 2/2009 | Saunier |
| 2001/0023514 | A1 | 9/2001 | Cottard et al. |
| 2002/0046431 | A1 | 4/2002 | Laurent et al. |
| 2002/0050013 | A1 | 5/2002 | Vidal et al. |
| 2002/0088062 | A1 | 7/2002 | Pratt |
| 2003/0019051 | A9 | 1/2003 | Vidal et al. |
| 2005/0166335 | A1 | 8/2005 | Vidal et al. |
| 2007/0006398 | A1 | 1/2007 | Hercouet |
| 2008/0005853 | A1 | 1/2008 | Cottard et al. |
| 2008/0016627 | A1 | 1/2008 | Cottard et al. |
| 2008/0016628 | A1 | 1/2008 | Cottard et al. |
| 2009/0007347 | A1 | 1/2009 | Cottard et al. |

FOREIGN PATENT DOCUMENTS

| CH | 421 343 | | 9/1966 |
| DE | 1 959 009 | | 12/1970 |
| DE | 23 59 399 | A1 | 6/1975 |
| DE | 38 43 892 | A1 | 6/1990 |
| DE | 41 33 957 | A1 | 4/1993 |
| DE | 101 48 847 | | 5/1997 |
| DE | 195 43 988 | A1 | 5/1997 |
| DE | 196 19 112 | | 11/1997 |
| EP | 0 770 375 | B1 | 5/1997 |
| EP | 0 873 745 | | 10/1998 |
| EP | 1 250 909 | | 10/2002 |
| EP | 1550 656 | A1 * | 6/2005 |
| EP | 1 550 656 | A1 | 7/2005 |
| FR | 2 586 913 | A1 | 3/1987 |
| FR | 2 733 749 | A1 | 11/1996 |
| FR | 2 750 048 | A1 | 12/1997 |
| FR | 2 801 308 | A1 | 5/2001 |
| FR | 2 886 132 | | 12/2006 |

(Continued)

OTHER PUBLICATIONS

French Search Report for FR 0652549, dated Mar. 6, 2007.
English language abstract of EP 0 770 375 B1, May 2, 1997.
English language abstract of JP 2-19576, Jan. 23, 1990.
English language abstract of JP 5-163124, Jun. 29, 1993.
Co-pending U.S. Appl. No. 10/999,999, filed Dec. 1, 2004.
Co-pending U.S. Appl. No. 11/812,603, filed Jun. 20, 2007.
Co-pending U.S. Appl. No. 11/812,610, filed Jun. 20, 2007.
Co-pending U.S. Appl. No. 11/898,438, filed Sep. 12, 2007.
Co-pending U.S. Appl. No. 11/987,450, filed Nov. 30, 2007.
Co-pending U.S. Appl. No. 11/987,451, filed Nov. 30, 2007.

(Continued)

*Primary Examiner* — Eisa B Elhilo
(74) *Attorney, Agent, or Firm* — Finnegan, Henderson, Farabow, Garrett & Dunner, L.L.P.

(57) ABSTRACT

Disclosed herein is a process for the predictable coloring of keratinous fibers, for example, human keratinous fibers, such as the hair, comprising applying to the fibers a first composition comprising at least one oxidation base derived from diamino-N,N-dihydropyrazolone and at least one coupler, mixed with a second composition chosen from "fundamental" and/or "golden fundamental" and/or "golden" compositions.

8 Claims, No Drawings

FOREIGN PATENT DOCUMENTS

| | | |
|---|---|---|
| FR | 2 886 135 | 12/2006 |
| FR | 2 886 136 | 12/2006 |
| FR | 2 886 137 | 12/2006 |
| FR | 2 886 138 | 12/2006 |
| FR | 2 886 139 | 12/2006 |
| FR | 2 886 140 | 12/2006 |
| FR | 2 886 141 | 12/2006 |
| FR | 2 886 142 | 12/2006 |
| FR | 2 902 323 | 12/2007 |
| FR | 2 902 327 | 12/2007 |
| FR | 2 902 328 | 12/2007 |
| GB | 1 005 233 | 9/1965 |
| GB | 1 026 978 | 4/1966 |
| GB | 1 153 196 | 5/1969 |
| GB | 1 486 576 | 9/1977 |
| JP | 2-19576 | 1/1990 |
| JP | 5-163124 | 6/1993 |
| JP | 2002-535312 | 10/2002 |
| WO | WO 94/08969 | 4/1994 |
| WO | WO 94/08970 | 4/1994 |
| WO | WO 96/15765 | 5/1996 |

OTHER PUBLICATIONS

English language Abstract of DE 1 959 009, dated Dec. 3, 1970.
English language Abstract of DE 101 48 847, dated May 10, 2003.
English language Abstract of DE 196 19 112, dated Nov. 13, 1997.
English language Abstract of EP 0 873 745, dated Oct. 28, 1998.
English language Abstract of EP 1 250 909, dated Oct. 23, 2002.
English language Abstract of FR 2 886 135, dated Dec. 1, 2006.
English language Abstract of FR 2 886 136, dated Dec. 1, 2006.
English language Abstract of FR 2 886 140, dated Dec. 1, 2006.
English language Abstract of FR 2 886 141, dated Dec. 1, 2006.
English language Abstract of FR 2 886 142, dated Dec. 1, 2006.
European Search Report for EP 07 12 1666, dated Apr. 2, 2008, (corresponding to co-pending U.S. Appl. No. 11/987,451).
French Search Report for FR 06/52557, dated Mar. 9, 2007.
French Search Report for FR 06/52558, dated Mar. 9, 2007.
French Search Report for FR 06/55213, dated Nov. 30, 2006.
French Search Report for FR 06/55214, dated Jul. 25, 2007.
Helvetica Chimica Acta., vol. XXXIII, Fasciculus V (1950), No. 152, pp. 1183-1194.
Morissette et al., Advanced Drug Delivery Reviews, 2004, 56, pp. 275-300.
Notice of Allowance mailed Jun. 26, 2007, in co-pending U.S. Appl. No. 10/999,999.
Notice of Allowance mailed Mar. 9, 2007, in co-pending U.S. Appl. No. 10/999,999.
Notice of rejection in counterpart Japanese Application No. 2004-348020, mailed Dec. 6, 2005.
Notice of rejection in counterpart Japanese Application No. 2004-348020, mailed Jan. 29, 2000.
Office Action mailed Apr. 16, 2009, in co-pending U.S. Appl. No. 11/812,610.
Office Action mailed Apr. 27, 2009, in co-pending U.S. Appl. No. 11/987,451.
Office Action mailed Aug. 4, 2008, in co-pending U.S. Appl. No. 11/812,603.
Office Action mailed Aug. 6, 2008, in co-pending U.S. Appl. No. 11/812,610.
Office Action mailed Mar. 2, 2009, in co-pending U.S. Appl. No. 11/898,438.
Office Action mailed Mar. 24, 2009, in co-pending U.S. Appl. No. 11/812,603.
Office Action mailed May 1, 2009, in co-pending U.S. Appl. No. 11/987,450.
Office Action mailed Oct. 27, 2008, in co-pending U.S. Appl. No. 11/987,450.
Office Action mailed Oct. 28, 2008, in co-pending U.S. Appl. No. 11/987,451.
STIC Search Report for U.S. Appl. No. 10/999,999, dated Dec. 13, 2006.
STIC Search Report for U.S. Appl. No. 11/812,603, dated Jul. 13, 2008.
STIC Search Report for U.S. Appl. No. 11/812,610, dated Jul. 31, 2008.
Vippagunta, S.R., "Crystalline Solids," Advanced Drug Delivery Reviews, 2001, 48, pp. 3-26.
Office Action mailed Dec. 11, 2009, in co-pending U.S. Appl. No. 11/987,451.

* cited by examiner

PROCESS FOR THE PREDICTABLE DYEING OF KERATINOUS FIBERS COMPRISING APPLYING AT LEAST ONE COMPOSITION COMPRISING AT LEAST ONE DIAMINO-N, N-DIHYDROPYRAZOLONE DERIVATIVE AND AT LEAST ONE COMPOSITION CHOSEN FROM FUNDAMENTAL AND/OR GOLDEN-HIGHLIGHTS COMPOSITIONS

This application claims benefit of U.S. Provisional Application No. 60/816,861, filed Jun. 28, 2006, the contents of which are incorporated herein by reference. This application also claims benefit of priority under 35 U.S.C. §119 to French Patent Application No. FR 0652549, filed Jun. 20, 2006, the contents of which are also incorporated herein by reference.

Disclosed herein is a process for the predictable coloring of keratinous fibers, for example, human keratinous fibers, such as the hair, comprising applying to the fibers at least one first composition comprising at least one oxidation base derived from diamino-N,N-dihydropyrazolone and at least one specific coupler, mixed with at least one second composition chosen from "fundamental" and/or "golden fundamental" and/or "golden" compositions.

It is known to dye keratinous fibers, for example, human keratinous fibers, such as the hair, with dyeing compositions comprising oxidation dye precursors, such as ortho- or para-phenylenediamines, ortho- or para-aminophenols, and heterocyclic compounds, such as diaminopyrazole derivatives, pyrazolo[1,5-a]pyrimidine derivatives, pyrimidine derivatives, pyridine derivatives, indole derivatives, and indoline derivatives, generally known as oxidation bases. Oxidation dye precursors or oxidation bases are colorless or weakly colored compounds which, in combination with oxidizing products, can give rise, by an oxidative coupling process, to colored or coloring compounds. Permanent colorings may thus be obtained.

It is also known that it is possible to vary the shades obtained with these oxidation bases by combining them with couplers or coloring modifiers, the latter being chosen, for instance, from meta-phenylenediamines, meta-aminophenols, meta-hydroxyphenols, and certain heterocyclic compounds.

The variety of the molecules available as oxidation bases and couplers may make it possible to obtain a rich palette of colors.

The use of oxidation bases, such as para-phenylenediamine and para-aminophenol derivatives, makes it possible to obtain a fairly broad range of colors at basic pH without, however, achieving shades of good chromaticity, while conferring on the hair excellent properties such as improved intensity of color, a variety of shades, and improved uniformity in the color and resistance to external agents.

In conventional oxidation dyeing processes, the professional or nonprofessional user, wishing to obtain predictable colors, can mix compositions of different shades in order to access the desired color, indeed even the desired intermediate shade. For example, it is expected that a "blond" dyeing composition mixed with a "coppery highlight" composition gives a "blond with coppery highlight" coloring to keratinous fibers. The advantage of these mixtures thus lies in the possibility of being able to predict the shaded coloring and thus of not limiting the creativity of the user.

However, certain oxidation dyeing precursors do not make it possible to achieve a predictable coloring as a mixture with another composition comprising "fundamental" and/or "golden fundamental" and/or "golden" shades. The result of the mixing of the dyeing compositions is risky or unpredictable. For instance, it proved to be the case that the result of color on the keratinous fibers was not very predictable, during mixings carried out by styling practitioners between the "coppery highlight" or "light red" shades and "fundamental" and/or "golden fundamental" and/or "golden" compositions, when one of the compositions comprises the coupler 6-chloro-2-methyl-5-aminophenol.

Thus, disclosed herein is a novel process for the coloring of keratinous fibers which makes possible a predictable coloring with varied, powerful, chromatic, attractive, and/or not very selective shades which is highly resistant to the various attacks which hair may be subjected to, such as shampoos, light, sweat, and/or permanent deformations.

In at least one embodiment, the process disclosed herein for coloring keratinous fibers comprises applying to the fibers a mixture of at least one dyeing composition (A) and at least one dyeing composition (B) chosen from "fundamental" and/or "golden fundamental" and/or "golden" compositions; wherein the dyeing composition (A) comprises at least one coupler 6-chloro-2-methyl-5-aminophenol and at least one oxidation base chosen from diamino-N,N-dihydropyrazolone derivatives of formula (I) and salts thereof,

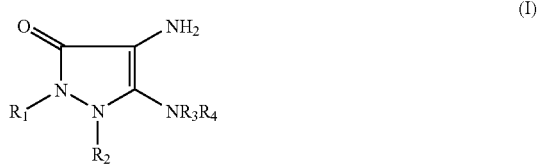

wherein:
$R_1$, $R_2$, $R_3$ and $R_4$, which may be identical or different, are chosen from:
linear and branched $C_1$-$C_6$ alkyl radicals optionally substituted by at least one radical chosen from $OR_5$ radicals, $NR_6R_7$ radicals, carboxyl radicals, sulpho radicals, carboxamido $CONR_6R_7$ radicals, sulphonamido $SO_2NR_6R_7$ radicals, and heteroaryl radicals and aryl radicals optionally substituted by at least one group chosen from ($C_1$-$C_4$)alkyl, hydroxyl, $C_1$-$C_2$ alkoxy, amino, and (di)($C_1$-$C_2$)alkylamino groups;
aryl radicals optionally substituted by at least one group chosen from ($C_1$-$C_4$)alkyl, hydroxyl, $C_1$-$C_2$ alkoxy, amino, and (di)($C_1$-$C_2$)alkylamino groups;
5- and 6-membered heteroaryl radicals optionally substituted by at least one radical chosen from ($C_1$-$C_4$) alkyl and ($C_1$-$C_2$)alkoxy radicals;
$R_3$ and $R_4$ may also be hydrogen;
$R_5$, $R_6$, and $R_7$, which may be identical or different, are chosen from:
hydrogen;
linear and branched $C_1$-$C_4$ alkyl radicals optionally substituted by at least one radical chosen from hydroxyl radicals, $C_1$-$C_2$ alkoxy radicals, carboxamido $CONR_8R_9$ radicals, sulphonyl $SO_2R_8$ radicals, and aryl radicals optionally substituted by at least one radical chosen from ($C_1$-$C_4$)alkyl, hydroxyl, $C_1$-$C_2$ alkoxy, amino, and (di)($C_1$-$C_2$)alkylamino radicals; and aryl radicals optionally substituted by at least one radical chosen from ($C_1$-$C_4$)alkyl, hydroxyl, $C_1$-$C_2$ alkoxy, amino, and (di)($C_1$-$C_2$)alkylamino radicals;
$R_6$ and $R_7$, which may be identical or different, may also be chosen from carboxamido $CONR_8R_9$ radicals and sulphonyl $SO_2R_8$ radicals;

$R_8$ and $R_9$, which may be identical or different, are chosen from hydrogen and linear and branched $C_1$-$C_4$ alkyl radicals optionally substituted by at least one group chosen from hydroxyl and $C_1$-$C_2$ alkoxy groups;

$R_1$ and $R_2$, on the one hand, and $R_3$ and $R_4$, on the other hand, may form, together with the nitrogen atom or atoms to which they are attached, a saturated or unsaturated 5- to 7-membered heterocycle optionally substituted by at least one radical chosen from halogen atoms, amino radicals, (di)($C_1$-$C_4$)alkylamino radicals, hydroxyl radicals, carboxyl radicals, and carboxamido radicals, ($C_1$-$C_2$)alkoxy radicals, and $C_1$-$C_4$ alkyl radicals optionally substituted by at least one radical chosen from hydroxyl, amino, (di)alkylamino, alkoxy, carboxyl, and sulphonyl radicals; and $R_3$ and $R_4$ may also form, together with the nitrogen atom to which they are attached, a 5- or 7-membered heterocycle, at least one carbon atom of which may optionally be replaced by at least one atom chosen from oxygen and optionally substituted nitrogen.

Unexpectedly, when the coupler of substituted meta-aminophenol type, such as 6-chloro-2-methyl-5-aminophenol, in the composition (A) is combined with at least one oxidation base of formula (I), such as 2,3-diamino-6,7-dihydro-1H,5H-pyrazolo[1,2-a]pyrazol-1-one, in the same composition (A), this makes it possible to obtain colorings which are predictable with regard to the color of the keratinous fibers, once mixed with a "fundamental" and/or "golden fundamental" and/or "golden" dyeing composition (B). The coloring obtained after the application of the mixture to the fibers is that expected, i.e., the keratinous fibers are colored with shades with "coppery" or "red" highlights.

Furthermore, this coloring may be powerful, attractive, not very selective, and/or resistant to the various attacks which hair may be subjected to, such as shampoos, light, sweat, and permanent deformations. The process disclosed herein may also make it possible to obtain intense and varied colorings at neutral pH, for example, natural shades.

As used herein,.the term "alkyl radical" is understood to mean a saturated, linear or branched hydrocarbon chain, for example, $C_1$-$C_{10}$, $C_1$-$C_6$, or $C_1$-$C_4$, hydrocarbon chains, such as methyl, ethyl, propyl, isopropyl, isobutyl, tert-butyl, pentyl, and hexyl radicals.

As used herein, the term "heteroatom" is understood to mean an atom chosen from oxygen, nitrogen, sulphur, and phosphorus.

As used herein, the term "halogen atom" is understood to mean an atom chosen from chlorine, bromine, iodine, and fluorine.

According to at least one embodiment, in the formula (I), the $R_1$ and $R_2$ radicals, which may be identical or different, may be chosen from:

$C_1$-$C_6$, for example, $C_1$-$C_4$, alkyl radicals optionally substituted by at least one group chosen from hydroxyl, ($C_1$-$C_2$)alkoxy, amino, and (di)($C_1$-$C_2$)alkylamino groups; and phenyl, methoxyphenyl, ethoxyphenyl, and benzyl radicals.

In another embodiment, the $R_1$ and $R_2$ radicals, which may be identical or different, may be chosen from methyl, ethyl, 2-hydroxyethyl, 3-hydroxypropyl, 2-hydroxypropyl, and phenyl radicals.

According to yet another embodiment, the $R_1$ and $R_2$ radicals may form, together with the nitrogen atoms to which they are attached, an optionally substituted, saturated or unsaturated, 5- or 6-membered ring.

For example, the $R_1$ and $R_2$ radicals may form, together with the nitrogen atoms to which they are attached, a ring chosen from pyrazolidine and pyridazolidine rings optionally substituted by at least one radical chosen from $C_1$-$C_4$ alkyl, hydroxyl, ($C_1$-$C_2$)alkoxy, carboxyl, carboxamido, amino, and (di)($C_1$-$C_2$)alkylamino radicals.

According to a further embodiment, the $R_1$ and $R_2$ radicals may form, together with the nitrogen atoms to which they are attached, a ring chosen from pyrazolidine and pyridazolidine rings.

In at least one embodiment, the $R_3$ and $R_4$ radicals, which may be identical or different, may be chosen from hydrogen; linear and branched $C_1$-$C_6$, for example, $C_1$-$C_4$, alkyl radicals optionally substituted by at least one radical chosen from hydroxyl, ($C_1$-$C_2$)alkoxy, amino, and (di)($C_1$-$C_2$)alkylamino radicals; and phenyl radicals optionally substituted by at least one radical chosen from hydroxyl, amino, and ($C_1$-$C_2$)alkoxy radicals.

According to another embodiment, the $R_3$ and $R_4$ radicals, which may be identical or different, may be chosen from hydrogen, methyl, ethyl, isopropyl, 2-hydroxyethyl, 3-hydroxypropyl, 2-hydroxypropyl, and 2-carboxyethyl. According to yet another embodiment, the $R_3$ and $R_4$ are hydrogen.

According to a further embodiment embodiment, the $R_3$ and $R_4$ radicals may form, together with the nitrogen atom to which they are attached, a 5- or 7-membered ring chosen from pyrrolidine, piperidine, homopiperidine, piperazine, and homopiperazine; it being possible for the rings to be substituted by at least one radical chosen from hydroxyl, amino, (di)($C_1$-$C_2$)alkylamino, carboxyl, carboxamido, and $C_1$-$C_4$ alkyl radicals, the $C_1$-$C_4$ alkyl radical optionally being substituted by at least one radical chosen from hydroxyl, amino, and (di)($C_1$-$C_2$)alkylamino radicals.

In still a further embodiment, the $R_3$ and $R_4$ radicals may form, together with the nitrogen atom to which they are attached, a 5- or 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-(hydroxymethyl)pyrrolidine, 3,4-dihydroxy-2-(hydroxymethyl)pyrrolidine, 3-hydroxypyrrolidine, 3,4-dihydroxypyrrolidine, 3-aminopyrrolidine, 3-(methylamino)pyrrolidine, 3-(dimethylamino)pyrrolidine, 4-amino-3-hydroxypyrrolidine, 3-hydroxy-4-[(2-hydroxyethyl)amino]pyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine, and N-(2-hydroxyethyl)homopiperazine.

According to another embodiment, the $R_3$ and $R_4$ radicals may form, together with the nitrogen atom to which they are attached, a 5- or 7-membered ring chosen from pyrrolidine, 3-hydroxypyrrolidine, 3-aminopyrrolidine, 3-(dimethylamino)pyrrolidine, pyrrolidine-2-carboxylic acid, 3-hydroxypyrrolidine-2-carboxylic acid, piperidine, hydroxypiperidine, homopiperidine, diazepane, N-methylhomopiperazine, and N-(β-hydroxyethyl)homopiperazine.

In accordance with a further embodiment, the $R_3$ and $R_4$ radicals may form, together with the nitrogen atom to which they are attached, a 5-membered ring, such as pyrrolidine, 3-hydroxypyrrolidine, 3-aminopyrrolidine, and 3-(dimethylamino)pyrrolidine.

The compounds of formula (I) may optionally be salified by at least one acid, for example, strong inorganic acids, such as HCl, HBr, HI, $H_2SO_4$, and $H_3PO_4$, and organic acids, such as acetic acid, lactic acid, tartaric acid, citric acid, succinic acid, benzenesulphonic acid, para-toluenesulphonic acid, formic acid, and ($C_1$-$C_4$ alkyl)$SO_3H$ acids, such as methanesulphonic acid.

The compounds of formula (I) may also be in the form of solvates, for example, hydrates and solvates of linear and branched alkyls, such as ethanol and isopropanol.

Non-limiting examples of derivatives of formula (I) include:

4,5-diamino-1,2-dimethyl-1,2-dihydropyrazol-3-one;
4-amino-5-methylamino-1,2-dimethyl-1,2-dihydropyrazol-3-one;
4-amino-5-dimethylamino-1,2-dimethyl-1,2-dihydropyrazol-3-one;
4-amino-5-(2-hydroxyethyl)amino-1,2-dimethyl-1,2-dihydropyrazol-3-one;
4-amino-5-(pyrrolidin-1-yl)-1,2-dimethyl-1,2-dihydropyrazol-3-one;
4-amino-5-(piperidin-1-yl)-1,2-dimethyl-1,2-dihydropyrazol-3-one;
4,5-diamino-1,2-di(2-hydroxyethyl)-1,2-dihydropyrazol-3-one;
4-amino-5-methylamino-1,2-di(2-hydroxyethyl)-1,2-dihydropyrazol-3-one;
4-amino-5-dimethylamino-1,2-di(2-hydroxyethyl)-1,2-dihydropyrazol-3-one;
4-amino-5-(2-hydroxyethyl)amino-1,2-di(2-hydroxyethyl)-1,2-dihydropyrazol-3-one;
4-amino-5-(pyrrolidin-1-yl)-1,2-di(2-hydroxyethyl)-1,2-dihydropyrazol-3-one;
4-amino-5-(piperidin-1-yl)-1,2-di(2-hydroxyethyl)-1,2-dihydropyrazol-3-one;
4,5-diamino-1,2-diethyl-1,2-dihydropyrazol-3-one;
4,5-diamino-1,2-phenyl-1,2-dihydropyrazol-3-one;
4,5-diamino-1-ethyl-2-methyl-1,2-dihydropyrazol-3-one;
4,5-diamino-2-ethyl-1-methyl-1,2-dihydropyrazol-3-one;
4,5-diamino-1-phenyl-2-methyl-1,2-dihydropyrazol-3-one;
4,5-diamino-2-phenyl-1-methyl-1,2-dihydropyrazol-3-one;
4,5-diamino-1-(2-hydroxyethyl)-2-methyl-1,2-dihydropyrazol-3-one;
4,5-diamino-2-(2-hydroxyethyl)-1-methyl-1,2-dihydropyrazol-3-one;
2,3-diamino-6,7-dihydro-1H,5H-pyrazolo[1,2-a]pyrazol-1-one;
2-amino-3-methylamino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(2-hydroxyethyl)amino-6,7-dihydro-1H,5H-pyrazolo[1,2-a]pyrazol-1-one;
2-amino-3-(2-hydroxypropyl)amino-6,7-dihydro-1H,5H-pyrazolo[1,2-a]pyrazol-1-one;
2-amino-3-bis[(2-hydroxyethyl)amino]-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
2-amino-3-(3-hydroxypyrrolidin-1-yl)-6,7-dihydro-1H,5H-pyrazolo[1,2-a]pyrazol-1-one;
2-amino-3-(piperidin-1-yl)-6,7-dihydro-1H,5H-pyrazolo[1,2-a]pyrazol-1-one;
2,3-diamino-6-hydroxy-6,7-dihydro-1H,5H-pyrazolo[1,2-a]pyrazol-1-one;
2,3-diamino-6-methyl-6,7-dihydro-1H,5H-pyrazolo[1,2-a]pyrazol-1-one;
2,3-diamino-6,6-dimethyl-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
2,3-diamino-5,8-dihydro-1H,6H-pyridazino[1,2-a]pyrazol-1-one;
4-amino-5-dimethylamino-1,2-diethyl-1,2-dihydropyrazol-3-one;
4-amino-1,2-diethyl-5-ethylamino-1,2-dihydropyrazol-3-one;
4-amino-1,2-diethyl-5-isopropylamino-1,2-dihydropyrazol-3-one;
4-amino-1,2-diethyl-5-(2-hydroxyethylamino)-1,2-dihydropyrazol-3-one;
4-amino-5-(2-dimethylaminoethylamino)-1,2-diethyl-1,2-dihydropyrazol-3-one;
4-amino-5-[bis(2-hydroxyethyl)amino]-1,2-diethyl-1,2-dihydropyrazol-3-one;
4-amino-1,2-diethyl-5-(3-(imidazol-1-yl)propylamino)-1,2-dihydropyrazol-3-one;
4-amino-5-dimethylamino-1,2-diethyl-1,2-dihydropyrazol-3-one;
4-amino-1,2-diethyl-5-ethylamino-1,2-dihydropyrazol-3-one;
4-amino-1,2-diethyl-5-isopropylamino-1,2-dihydropyrazol-3-one;
4-amino-1,2-diethyl-5-(2-hydroxyethylamino)-1,2-dihydropyrazol-3-one;
4-amino-5-(2-dimethylaminoethylamino)-1,2-diethyl-1,2-dihydropyrazol-3-one;
4-amino-5-[bis(2-hydroxyethyl)amino]-1,2-diethyl-1,2-dihydropyrazol-3-one;
4-amino-1,2-diethyl-5-(3-(imidazol-1-yl)propylamino)-1,2-dihydropyrazol-3-one;
4-amino-1,2-diethyl-5-(3-hydroxypyrrolidin-1-yl)-1,2-dihydropyrazol-3-one;
4-amino-1,2-diethyl-5-(pyrrolidin-1-yl)-1,2-dihydropyrazol-3-one;
4-amino-5-(3-dimethylaminopyrrolidin-1-yl)-1,2-diethyl-1,2-dihydropyrazol-3-one;
4-amino-1,2-diethyl-5-(4-methylpiperazin-1-yl)pyrazolidin-3-one;
2,3-diamino-6-hydroxy-6,7-dihydro-5H-pyrazolo[1,2-a]pyrazol-1-one; and the addition salts thereof, some of which are represented below in order to illustrate the names by the chemical structures:

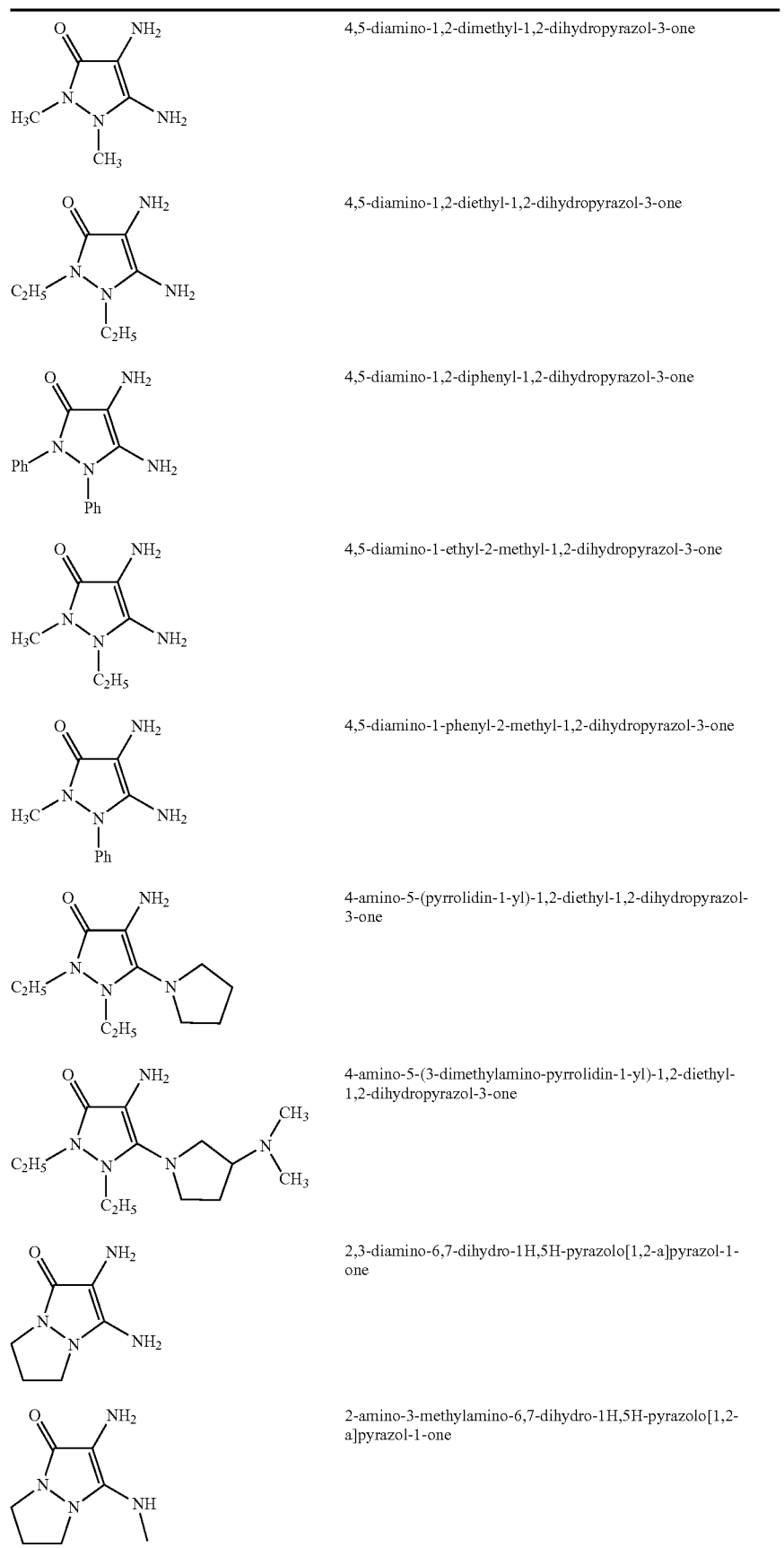

4,5-diamino-1,2-dimethyl-1,2-dihydropyrazol-3-one 4,5-diamino-1,2-diethyl-1,2-dihydropyrazol-3-one 4,5-diamino-1,2-diphenyl-1,2-dihydropyrazol-3-one 4,5-diamino-1-ethyl-2-methyl-1,2-dihydropyrazol-3-one 4,5-diamino-1-phenyl-2-methyl-1,2-dihydropyrazol-3-one 4-amino-5-(pyrrolidin-1-yl)-1,2-diethyl-1,2-dihydropyrazol-3-one 4-amino-5-(3-dimethylamino-pyrrolidin-1-yl)-1,2-diethyl-1,2-dihydropyrazol-3-one 2,3-diamino-6,7-dihydro-1H,5H-pyrazolo[1,2-a]pyrazol-1-one 2-amino-3-methylamino-6,7-dihydro-1H,5H-pyrazolo[1,2-a]pyrazol-1-one -continued

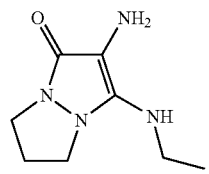
2-amino-3-ethylamino-6,7-dihydro-1H,5H-pyrazolo[1,2-a]pyrazol-1-one

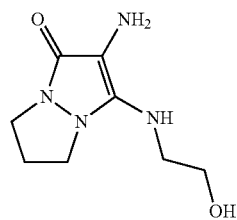
2-amino-3-(2-hydroxyethyl)amino-6,7-dihydro-1H,5H-pyrazolo[1,2-a]pyrazol-1-one

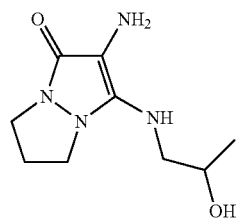
2-amino-3-(2-hydroxypropyl)amino-6,7-dihydro-1H,5H-pyrazolo[1,2-a]pyrazol-1-one

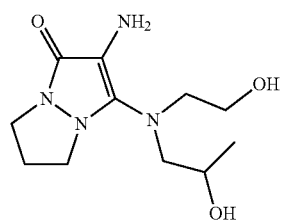
2-amino-3-[bis(2-hydroxyethyl)amino]-6,7-dihydro-1H,5H-pyrazolo[1,2-a]pyrazol-1-one

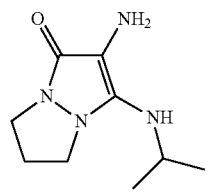
2-amino-3-isopropylamino-6,7-dihydro-1H,5H-pyrazolo[1,2-a]pyrazol-1-one

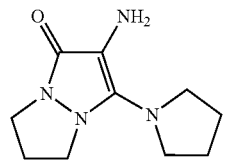
2-amino-3-(pyrrolidin-1-yl)-6,7-dihydro-1H,5H-pyrazolo[1,2-a]pyrazol-1-one

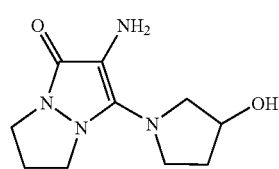
2-amino-3-(3-hydroxypyrrolidin-1-yl)-6,7-dihydro-1H,5H-pyrazolo[1,2-a]pyrazol-1-one

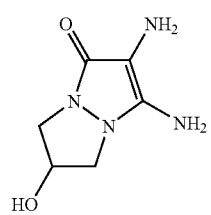
2,3-diamino-6-hydroxy-6,7-dihydro-1H,5H-pyrazolo[1,2-a]pyrazol-1-one

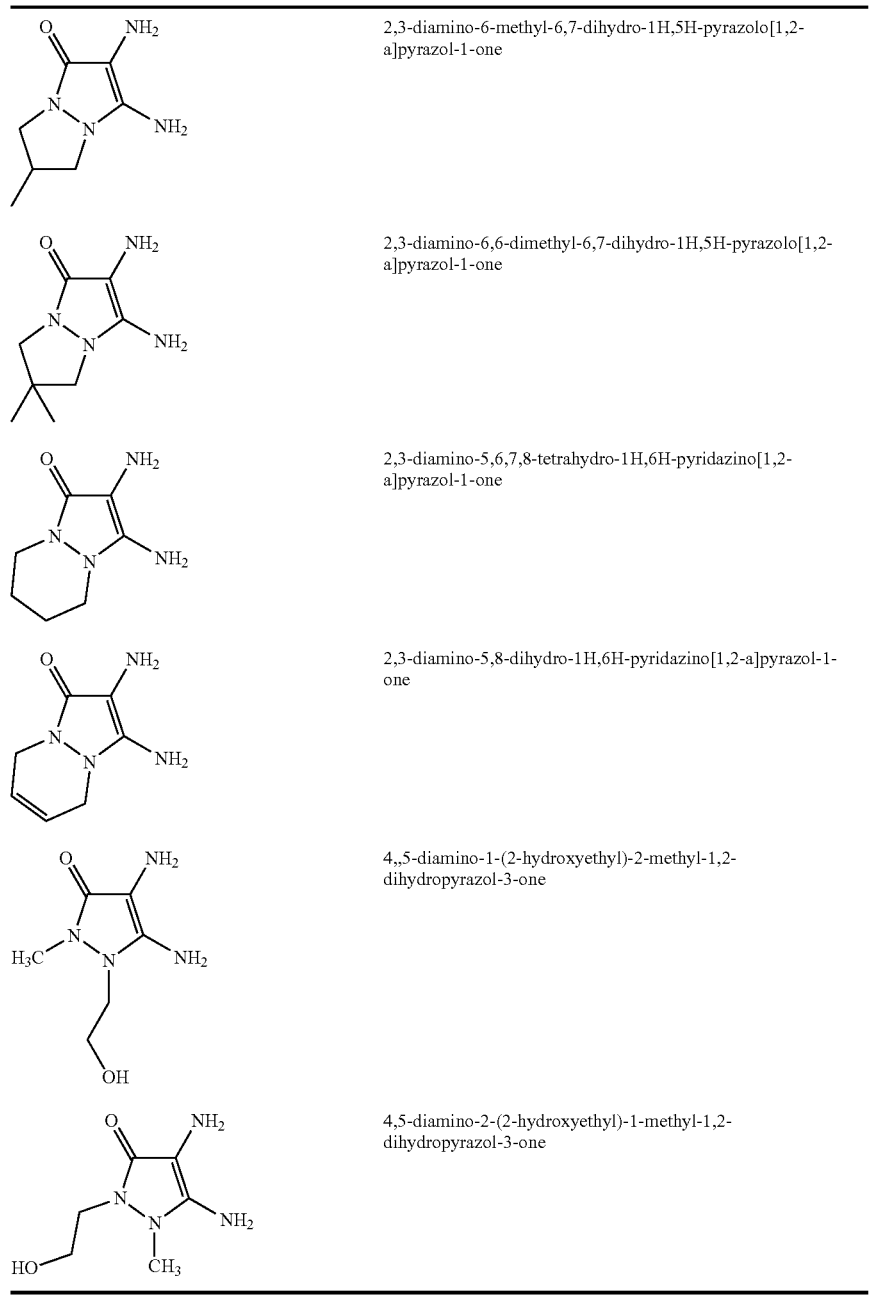

2,3-diamino-6-methyl-6,7-dihydro-1H,5H-pyrazolo[1,2-a]pyrazol-1-one 2,3-diamino-6,6-dimethyl-6,7-dihydro-1H,5H-pyrazolo[1,2-a]pyrazol-1-one 2,3-diamino-5,6,7,8-tetrahydro-1H,6H-pyridazino[1,2-a]pyrazol-1-one 2,3-diamino-5,8-dihydro-1H,6H-pyridazino[1,2-a]pyrazol-1-one 4,,5-diamino-1-(2-hydroxyethyl)-2-methyl-1,2-dihydropyrazol-3-one 4,5-diamino-2-(2-hydroxyethyl)-1-methyl-1,2-dihydropyrazol-3-one According to at least one embodiment, the diamino-N,N-dihydropyrazolone derivatives of formula (I) and the addition salts thereof may be chosen from:
2,3-diamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
4,5-diamino-1,2-dimethyl-1,2-dihydropyrazol-3-one;
4,5-diamino-1,2-diethyl-1,2-dihydropyrazol-3-one;
4,5-diamino-1,2-di(2-hydroxyethyl)-1,2-dihydropyrazol-3-one;
2-amino-3-(2-hydroxyethyl)amino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
4-amino-1,2-diethyl-5-(pyrrolidin-1-yl)-1,2-dihydro-pyrazol-3-one;
4-amino-5-(3-dimethylaminopyrrolidin-1-yl)-1,2-diethyl-1,2-dihydropyrazol-3-one; and
2,3-diamino-6-hydroxy-6,7-dihydro-1H,5H-pyrazolo[1,2-a]pyrazol-1-one.

In another embodiment, the at least one compound of formula (I) may be chosen from 2,3-diamino-6,7-dihydro-1H,5H-pyrazolo[1,2-a]pyrazol-1-one and the addition salts thereof.

The composition (A) comprises at least one coupler of halogenated substituted meta-aminophenol type chosen from 6-chloro-2-methyl-5-aminophenol and the addition salts thereof.

According to one embodiment, the at least one coupler is present in the dyeing composition (A) in an amount ranging from 0.001 to 8%, or from 0.1 to 5%, relative to the total weight of the dyeing composition (A).

In another embodiment, the at least one oxidation base of formula (I) is present in the dyeing composition (A) in an amount, for each of them, ranging from 0.001 to 8% by weight, relative to the total weight of the dyeing composition (A), for example, ranging from 0.1 to 5%.

In at least one embodiment as disclosed herein is a composition (A) of coppery shade, in which the molar ratio of the oxidation base of formula (I), for instance, 2,3-diamino-6,7-dihydro-1H,5H-pyrazolo[1,2-a]pyrazol-1-one, to the coupler, for instance, 6-chloro-2-methyl-5-aminophenol, is less than 1. In at least one embodiment, the ratio ranges from 0.5 to 0.95.

In another embodiment, the composition (A) of coppery shade comprises another coupler, for instance, a nonhalogenated substituted meta-aminophenol coupler, such as 2-methyl-5-aminophenol, for which the molar ratio of the oxidation base of formula (I), for example, 2,3-diamino-6,7-dihydro-1H,5H-pyrazolo[1,2-a]pyrazol-1-one, to the additional coupler is greater than 1. According to one embodiment, the ratio ranges from 2 to 5.

The composition (A) may further comprise other oxidation bases and other couplers different from those disclosed above and conventionally used for the dyeing of keratinous fibers.

The composition (A) of the present disclosure can, for example, comprise at least one additional oxidation base chosen from para-phenylenediamines, bisphenylalkylenediamines, para-aminophenols, bis-para-aminophenols, ortho-aminophenols, ortho-phenylenediamines, heterocyclic bases other than the derivatives of formula (I) as defined above, and the addition salts thereof.

Non-limiting examples of para-phenylenediamines include para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N, N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxyethyl)-para-phenylenediamine, N-(β, γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 4-aminophenylpyrrolidine, 2-thienyl-para-phenylenediamine, 2-(β-hydroxyethylamino)-5-aminotoluene, 3-hydroxy-1-(4'-aminophenyl)pyrrolidine, and the acid addition salts thereof.

According to one embodiment, the para-phenylenediamines may be chosen, for example, from para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine, and the acid addition salts thereof.

Examples of bisphenylalkylenediamines include, but are not limited to, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-amino-phenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the acid addition salts thereof.

Suitable para-aminophenols may be chosen, for example, from para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-((β-hydroxyethyl)aminomethyl)phenol, 4-amino-2-fluorophenol, and the acid addition salts thereof.

Non-limiting examples of ortho-aminophenols include 2-aminophenol, 2-amino-5-methylphenol, 2-amino-6-methylphenol, 5-acetamido-2-aminophenol, and the acid addition salts thereof.

Examples of heterocyclic bases include, but are not limited to, pyridine derivatives, pyrimidine derivatives, and pyrazole derivatives.

Suitable pyridine derivatives may be chosen, for instance, from the compounds disclosed, for example, in British Patent Nos. 1 026 978 and 1 153 196, such as 2,5-diaminopyridine, 2-[(4-methoxyphenyl)amino]-3-aminopyridine, 2,3-diamino-6-methoxypyridine, 2-[(β-methoxyethyl)amino]-3-amino-6-methoxypyridine, 3,4-diaminopyridine, and the acid addition salts thereof.

Other examples of pyridine oxidation bases include, but are not limited to, 3-aminopyrazolo[1,5-a]pyridine oxidation bases and the addition salts thereof, for example, those disclosed in French Patent Application No. 2 801 308. Such oxidation bases may include, for instance, pyrazolo[1,5-a]pyridin-3-ylamine; 2-(acetylamino)-pyrazolo[1,5-a]pyridin-3-ylamine; 2-(morpholin-4-yl)pyrazolo[1,5-a]pyridin-3-ylamine; 3-aminopyrazolo[1,5-a]pyridine-2-carboxylic acid; 2-methoxypyrazolo[1,5-a]pyridin-3-ylamine; (3-aminopyrazolo[1,5-a]pyridin-7-yl)methanol; 2-(3-aminopyrazolo[1,5-a]pyridin-5-yl)ethanol; 2-(3-aminopyrazolo[1,5-a]pyridin-7-yl)ethanol; (3-aminopyrazolo[1,5-a]pyridin-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-(morpholin-4-yl)pyrazolo[1,5-a]pyridin-3-ylamine; pyrazolo[1,5-a]pyridine-3,5-diamine; 5-(morpholin-4-yl)pyrazolo[1,5-a]pyridin-3-ylamine; 2-[(3-aminopyrazolo[1,5-a]pyridin-5-yl)(2-hydroxyethyl)amino]ethanol; 2-[(3-amino-pyrazolo[1,5-a]pyridin-7-yl)(2-hydroxyethyl)amino]ethanol; 3-aminopyrazolo[1,5-a]pyridin-5-ol; 3-aminopyrazolo[1,5-a]pyridin-4-ol; 3-aminopyrazolo[1,5-a]pyridin-6-ol; 3-aminopyrazolo[1,5-a]pyridin-7-ol; and the acid and base addition salts thereof.

Non-limiting examples of pyrimidine derivatives include those described, for example, in German Patent No. 23 59 399; Japanese Patent Application No. 88-169571; Japanese Patent No. 05-63124; European Patent No. 0 770 375, and International Patent Application Publication No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, and 2,5,6-triaminopyrimidine, and pyrazolopyrimidine derivatives, such as those described in French Patent Application No. 2 750 048, for example, pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-amino-pyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl) amino]ethanol, 2-[(7-aminopyrazolo[1,5-a]pyrimidin-3-yl) (2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-(imidazolylpropylamino)pyrazolo[1,5-a]pyrimidine, the acid addition salts thereof and the tautomeric forms thereof, when a tautomeric equilibrium exists.

Examples of suitable pyrazole derivatives include, but are not limited to, the compounds disclosed in German Patent Nos. 38 43 892 and 41 33 957, International Patent Application Publication Nos. WO 94/08969 and WO 94/08970, French Patent Application No. 2 733 749, and German Patent Application No.195 43 988, such as 4,5-diamino-1-methylpyrazole, 4,5-diamino-1-($\beta$-hydroxyethyl)pyrazole, 3,4-diamino-pyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-(tert-butyl)-1-methylpyrazole, 4,5-diamino-1-(tert-butyl)-3-methylpyrazole, 4,5-diamino-1-($\beta$-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino) pyrazole, 3,5-diamino-4-($\beta$-hydroxyethyl)amino-1-methylpyrazole, and the acid addition salts thereof.

The at least one additional oxidation base may be present in the dyeing composition (A) in an amount, for each of them, ranging from 0.001 to 10% by weight, relative to the total weight of the dyeing composition (A), for instance, ranging from 0.005 to 6%.

The dyeing composition (A) may further comprise at least one additional coupler other than 6-chloro-2-methyl-5-aminophenol and the addition salts thereof.

According to one embodiment, the at least one additional coupler may be chosen from meta-phenylenediamines, meta-aminophenols, meta-diphenols, naphthalene couplers, heterocyclic couplers, and the addition salts thereof.

Non-limiting examples of meta-aminophenols include 3-aminophenol, 5-amino-2-methoxyphenol, 5-amino-2-($\beta$-hydroxyethyloxy)phenol, 5-amino-2-methylphenol, 5-N-($\beta$-hydroxyethyl)amino-2-methylphenol, 5-N-($\beta$-hydroxyethyl) amino-4-methoxy-2-methylphenol, 5-amino-4-methoxy-2-methylphenol, 5-amino-4-chloro-2-methylphenol, 5-amino-2,4-dimethoxyphenol, 5-($\gamma$-hydroxypropylamino)-2-methylphenol, 3-(dimethylamino)phenol; 2-methyl-5-(dimethylamino)phenol, 2-ethyl-5-(dimethyl-amino)phenol, 2-methoxy-5-(dimethylamino)phenol, 2-ethoxy-5-(dimethylamino)phenol, 2-($\beta$-hydroxyethyl)-5-(dimethylamino)phenol, 3-(diethylamino)phenol, 2-methyl-5-(diethylamino) phenol, 2-ethyl-5-(diethylamino)phenol, 2-methoxy-5-(diethylamino)phenol, 2-ethoxy-5-(diethylamino)phenol, 2-($\beta$-hydroxyethyl)-5-(diethylamino)phenol, 3-[di($\beta$-hydroxyethyl)amino]phenol, 2-methyl-5-[di($\beta$-hydroxyethyl) amino]phenol, 2-ethyl-5-[di($\beta$-hydroxyethyl)amino]phenol, 2-methoxy-5-[di($\beta$-hydroxyethyl)amino]phenol, 2-ethoxy-5-[di($\beta$-hydroxyethyl)amino]phenol, 2-($\beta$-hydroxyethyl)-5-[di($\beta$-hydroxyethyl)amino]phenol, 3-(pyrrolidin-1-yl)phenol, 2-methyl-5-(pyrrolidin-1-yl)phenol, 2-ethyl-5-(pyrrolidin-1-yl)phenol, 2-methoxy-5-(pyrrolidin-1-yl) phenol, 2-ethoxy-5-(pyrrolidin-1-yl)phenol, 2-($\beta$-hydroxyethyl)-5-(pyrrolidin-1-yl)phenol, 3-(piperidin-1-yl) phenol, 2-methyl-5-(piperidin-1-yl)phenol, 2-ethyl-5-(piperidin-1-yl)phenol, 2-methoxy-5-( piperidin-1-yl) phenol, 2-ethoxy-5-(piperidin-1-yl)phenol, 2-($\beta$-hydroxyethyl)-5-(piperidin-1-yl)phenol, 3-(piperazin-1-yl) phenol, 2-methyl-5-(piperazin-1-yl)phenol, 2-ethyl-5-(piperazin-1-yl)phenol, 2-methoxy-5-(piperazin-1-yl) phenol, 2-ethoxy-5-(piperazin-1-yl) phenol, 2-($\beta$-hydroxyethyl)-5-(piperazin-1-yl)phenol, 3-(4-methylpiperazin-1-yl)phenol, 2-methyl-5-(4-methylpiperazin-1-yl)phenol, 2-ethyl-5-(4-methylpiperazin-1-yl)phenol, 2-methoxy-5-(4-methylpiperazin-1-yl)phenol, 2-ethoxy-5-(4-methylpiperazin-1-yl)phenol, 2-($\beta$-hydroxyethyl)-5-(4-methylpiperazin-1-yl)phenol, 3-(4-ethylpiperazin-1-yl)phenol, 2-methyl-5-(4-ethylpiperazin-1-yl)phenol, 2-ethyl-5-(4-ethylpiperazin-1-yl)phenol, 2-methoxy-5-(4-ethylpiperazin-1-yl)phenol, 2-ethoxy-5-(4-ethylpiperazin-1-yl)phenol, 2-($\beta$-hydroxyethyl)-5-(4-ethylpiperazin-1-yl) phenol, 3-(4-($\beta$-hydroxyethyl)piperazin-1-yl)phenol, 2-methyl-5-(4-($\beta$-hydroxyethyl)piperazin-1-yl)phenol, 2-ethyl-5-(4-($\beta$-hydroxyethyl)piperazin-1-yl)phenol, 2-methoxy-5-(4-($\beta$-hydroxyethyl)piperazin-1-yl)phenol, 2-ethoxy-5-(4-($\beta$-hydroxyethyl)piperazin-1-yl)phenol, 2-($\beta$-hydroxyethyl)-5-(4-($\beta$-hydroxyethyl)piperazin-1-yl)phenol, 3-(morpholin-4-yl)phenol, 2-methyl-5-(rmorpholin-4-yl) phenol, 2-ethyl-5-(morpholin-4-yl)phenol, 2-methoxy-5-(morpholin-4-yl)phenol, 2-ethoxy-5-(morpholin-4-yl)phenol, 2-($\beta$-hydroxyethyl)-5-(morpholin-4-yl)phenol, and the addition salts thereof.

Examples of couplers other than meta-aminophenols that may be used include, but are not limited to, 1,3-dihydroxybenzene, 1,3-dihydroxy-2-methylbenzene, 4-chloro-1,3-dihydroxybenzene, 2,4-diamino-1-(P-hydroxyethyloxy)benzene, 2-amino-4-($\beta$-hydroxyethylamino)-1-methoxybenzene, 1,3-diaminobenzene, 1,3-bis(2,4-diaminophenoxy)propane, 3-ureidoaniline, 3-ureido-1-(dimethylamino)benzene, sesamol, 1-$\beta$-hydroxyethylamino-3,4-methylenedioxybenzene, $\alpha$-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-($\beta$-hydroxyethyl)amino-3,4-methylenedioxybenzene, 2,6-bis($\beta$-hydroxyethylamino)toluene, and the acid addition salts thereof.

According to at least one embodiment, the addition salts of the oxidation bases and couplers which can be used in the context of the present disclosure may be chosen, for example, from acid addition salts, such as hydrochlorides, hydrobromides, sulphates, citrates, succinates, tartrates, lactates, tosylates, benzenesulphonates, alkyltosylates, phosphates and acetates, and base addition salts, such as sodium hydroxide, potassium hydroxide, aqueous ammonia, amines, and alkanolamines.

The dyeing composition (A) in accordance with the present disclosure may further comprise at least one direct dye which may be chosen, for example, from nitrobenzene dyes, azo direct dyes, and methine direct dyes. These direct dyes may be chosen from nonionic, anionic, and cationic direct dyes.

As used herein, the terms "fundamental" or "golden fundamental" or "golden" dyeing composition is understood to mean any composition comprising at least one oxidation base and optionally at least one coupler resulting, on keratinous fibers, in a "fundamental" or "golden fundamental" or "golden" shade, i.e. a shade which can, for example, be defined by the following general formula:

wherein:
- H is the level of tone of the shade as defined in the work *The Science of Hair Care*, $2^{nd}$ edition, published by Taylor and Francis Group, 2005, pp. 295, and H can, according to the work, range from 1 to 10; and, according to the present disclosure H may range from 4 to 9; for example, from 6 to 9, or from 7 to 9;
- $R_1$ is the primary or dominant highlight with $R_1=1$ corresponding to the ash highlight, $R_1=2$: iridescent highlight, $R_1=3$: golden highlight, $R_1=4$: coppery highlight, $R_1=5$: mahogany highlight, $R_1=6$: red highlight, and $R_1=7$: green highlight; $R_1$ according to the present disclosure is equal to 3;
- $R_2$ is the secondary or correcting highlight;
- n is equal to 0 or 1; when n represents 1, the sign 0 softens the strength of the $R_1$ (and $R_2$) highlight;
- $n_1$ is equal to 0 or 1; and
- $n_2$ is equal to 0 or 1; when $n_2$ represents 1, $R_2$ can take each of the values from 1 to 7 mentioned above.

Examples of fundamental or golden fundamental or golden shades according to the present disclosure include, but are not limited to, the shades 7-8-9-7.03-8.03-9.03-7.3-8.3-9.3.

According to one embodiment, no is equal to 1. In another embodiment, $n_1$ is equal to 1 and n is equal to zero.

According to at least one embodiment, the "fundamental" or "golden fundamental" or "golden" composition is chosen so that, in the presence of an oxidizing agent, it results, at ambient temperature on a lock of unpermed grey hair comprising 90% of white hairs, in the following values in the L*a*b* calorimetric system: a* is in the range [0; +20], b* is in the range [0; +20], and L* is in the range [0; +50].

In one embodiment, the composition (B) is a "fundamental" composition (B) having the following L*a*b* values: a* is in the range [0; +6], b* is in the range [+10; +15], and L* is in the range [+20; +50].

In another embodiment, the composition (B) is a "golden fundamental" composition having the following L*a*b* values:
a* is in the range [+6; +10], b* is in the range [+15; +20], and L* is in the range [+20; +50].

That at least one oxidation base present in the composition (B) and the at least one coupler optionally present in the composition (B) may be chosen from those defined above as additional bases and couplers of the composition (A).

According to at least one embodiment, the composition (B) does not comprise compounds of formula (I) and the addition salts thereof or 6-chloro-2-methyl-5-aminophenol and the addition salts thereof.

In another embodiment, the composition (B) comprises at least one oxidation base chosen from para-phenylenediamines, such as para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine, and the acid addition salts thereof. According to a further embodiment, the at least one oxidation base optionally present in composition (B) is chosen from para-toluenediamine, para-phenylenediamine, and the addition salts thereof.

In yet another embodiment, the at least one oxidation base may be present in composition (B) in an amount less than or equal to 5 mmol per 100 g of composition (B).

According to a further embodiment, composition (B) may comprise at least one coupler chosen from meta-diphenols, such as 1,3-dihydroxybenzene, meta-aminophenols, such as 3-aminophenol, and meta-phenylenediamines, such as 2,4-diamino-1-(β-hydroxyethyloxy)benzene.

The medium appropriate for dyeing, also referred to as dyeing vehicle, is a cosmetic medium chosen from water and mixtures of water and at least one organic solvent in order to dissolve the compounds which would not be sufficiently soluble in water. Examples of suitable organic solvents include, but are not limited to, lower $C_1$-$C_4$ alkanols, such as ethanol and isopropanol; polyols and polyol ethers, such as 2-butoxyethanol, propylene glycol, propylene glycol monomethyl ether, diethylene glycol monoethyl ether, and diethylene glycol monomethyl ether; and aromatic alcohols, such as benzyl alcohol and phenoxyethanol, and mixtures thereof.

The at least one organic solvent may be present in the dyeing compositions in an amount ranging from 1 to 40% by weight, relative to the total weight of dyeing compositions (A) and (B), for example, from 5 to 30% by weight.

The dyeing compositions (A) and/or (B) may further comprise at least one adjuvant conventionally used in compositions for dyeing the hair, such as anionic, cationic, nonionic, amphoteric, and zwitterionic surface-active agents and mixtures thereof; anionic, cationic, nonionic, amphoteric, and zwitterionic polymers and mixtures thereof, inorganic and organic thickening agents, such as anionic, cationic, nonionic, and amphoteric polymeric associative thickeners; antioxidants; penetration agents; sequestering agents; fragrances; buffers; dispersing agents; conditioning agents, such as volatile and/or nonvolatile and modified and/or unmodified silicones; film-forming agents; ceramides; preservatives; and opacifying agents.

The at least one adjuvant may be present in the compositions in an amount, for each of them, ranging from 0.01 to 20% by weight relative to the total weight of the dyeing compositions (A) and/or (B).

It is to be understood that a person skilled in the art will take care to choose the at least one optional additional ingredients so that the beneficial properties intrinsically associated with the dyeing compositions (A) and (B) in accordance with the present disclosure are not, or not substantially, detrimentally affected by the envisaged addition or additions.

The pH of the dyeing compositions (A) and/or (B) may range, for example, from 3 and 12, for example, from 5 to 11. The pH can be adjusted to the desired value using acidifying or basifying agents generally used in dyeing keratinous fibers or else using conventional buffering systems.

Non-limiting examples of acidifying agents include inorganic and organic acids, such as hydrochloric acid, orthophosphoric acid, sulphuric acid, carboxylic acids, such as acetic acid, tartaric acid, citric acid, and lactic acid, and sulphonic acids.

Examples of basifying agents include, but are not limited to, aqueous ammonia, alkaline carbonates, alkanolamines, such as mono-, di- and triethanolamines and their derivatives, sodium hydroxide, potassium hydroxide, and compounds of formula (III):

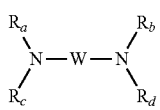

wherein W is a propylene residue optionally substituted by at least one radical chosen from hydroxyl and $C_1$-$C_4$ alkyl radicals, and $R_a$, $R_b$, $R_c$, and $R_d$, which may be identical or different, are chosen from hydrogen, $C_1$-$C_4$ alkyl radicals, and $C_1$-$C_4$ hydroxyalkyl radicals.

The dyeing compositions (A) and/or (B) can be provided in various forms, such as liquids, creams, and gels or in any other form appropriate for carrying out dyeing of keratinous fibers such as human hair.

According to at least one embodiment, the mixture of the two compositions (A) and (B) may be in a ratio (A)/(B) by weight ranging from 5/1 to 1/5, for example, from 3/1 to 1/3. In another embodiment, the ratio by weight of the (A)/(B) mixture is 1/1.

The mixture can be prepared before or at the time of application to keratinous fibers.

Disclosed herein is a process for coloring keratinous fibers comprising applying, to the fibers, a mixture of a composition (A) and of a composition (B) chosen from "fundamental" and "golden fundamental" compositions, wherein composition (A) comprises at least one coupler chosen from 6-chloro-2-methyl-5-aminophenol and salts thereof and at least one oxidation base chosen from diamino-N,N-dihydropyrazolone derivatives of formula (I) and salts thereof,

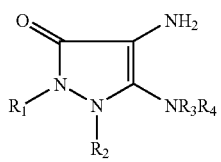

wherein:
$R_1$, $R_2$, $R_3$, and $R_4$, which may be identical or different, are chosen from:
  linear and branched $C_1$-$C_6$ alkyl radicals optionally substituted by at least one radical chosen from $OR_5$ radicals, $NR_6R_7$ radicals, carboxyl radicals, sulpho radicals, carboxamido $CONR_6R_7$ radicals, sulphonamido $SO_2NR_6R_7$ radicals, heteroaryl and aryl radicals optionally substituted by at least one group chosen from $(C_1$-$C_4)$alkyl, hydroxyl, $C_1$-$C_2$ alkoxy, amino, and $(di)(C_1$-$C_2)$alkylamino groups;
  aryl radicals optionally substituted by at least one group chosen from $(C_1$-$C_4)$alkyl, hydroxyl, $C_1$-$C_2$ alkoxy, amino, and $(di)(C_1$-$C_2)$alkylamino groups;
  5- or 6-membered heteroaryl radicals optionally substituted by at least one radical chosen from $(C_1$-$C_4)$alkyl and $(C_1$-$C_2)$alkoxy;
$R_3$ and $R_4$ can also be hydrogen;
$R_5$, $R_6$, and $R_7$, which may be identical or different, are chosen from:
  hydrogen; and
  linear and branched $C_1$-$C_4$ alkyl radicals optionally substituted by at least one radical chosen from hydroxyl radicals, $C_1$-$C_2$ alkoxy radicals, carboxamido $CONR_8R_9$ radicals, sulphonyl $SO_2R_8$ radicals, aryl radicals optionally substituted by at least one group chosen from $(C_1$-$C_4)$alkyl, hydroxyl, $C_1$-$C_2$ alkoxy, amino, and $(di)(C_1$-$C_2)$alkylamino; and aryl radicals optionally substituted by at least one group chosen from $(C_1$-$C_4)$alkyl, hydroxyl, $C_1$-$C_2$ alkoxy, amino, and $(di)(C_1$-$C_2)$alkylamino;
$R_6$ and $R_7$, which may be identical or different, can also be chosen from carboxamido $CONR_8R_9$ radicals and sulphonyl $SO_2R_8$ radicals;
$R_8$ and $R_9$, which may be identical or different, are chosen from hydrogen and linear and branched $C_1$-$C_4$ alkyl radicals optionally substituted by at least one group chosen from hydroxyl and $C_1$-$C_2$ alkoxy groups;
$R_1$ and $R_2$, on the one hand, and $R_3$ and $R_4$, on the other hand, may form, together with the nitrogen atom or atoms to which they are attached, a saturated or unsaturated 5- to 7-membered heterocycle optionally substituted by at least one radical chosen from halogen atoms, amino radicals, $(di)(C_1$-$C_4)$alkylamino radicals, hydroxyl radicals, carboxyl radicals, and carboxamido, $(C_1$-$C_2)$alkoxy radicals, and $C_1$-$C_4$ alkyl radicals optionally substituted by at least one radical chosen from hydroxyl, amino, (di)alkylamino, alkoxy, carboxyl, and sulphonyl radicals;
$R_3$ and $R_4$ may also form, together with the nitrogen atom to which they are attached, a 5- or 7-membered heterocycle, the carbon atoms of which may optionally be replaced by at least one atom chosen from oxygen and optionally substituted nitrogen.

According to one embodiment, the mixture of the compositions (A) and (B) is added at the time of use to a composition comprising, in a medium appropriate for dyeing, at least one oxidizing agent, the at least one oxidizing agent being present in an amount sufficient to develop a coloring. The mixture obtained may be subsequently applied to the keratinous fibers. After a leave-in time ranging, for example, from 3 to 50 minutes, such as from 5 to 30 minutes, or 20 minutes, the keratinous fibers may be rinsed, washed with a shampoo, rinsed again, and then dried.

Oxidizing agents conventionally used for the oxidation dyeing of keratinous fibers include, for example, hydrogen peroxide, urea hydrogen peroxide, alkali metal bromates, persalts, such as perborates and persulphates, peracids and oxidase enzymes, for example, peroxidises, 2-electron oxidoreductases, such as uricases, and 4-electron oxygenases, such as laccases. According to one embodiment, the at least one oxidizing agent is hydrogen peroxide.

The oxidizing composition may further comprise at least one adjuvant conventionally used in compositions for dyeing the hair and defined above.

The pH of the oxidizing composition including the at least one oxidizing agent is such that, after mixing with the dyeing composition, the pH of the resulting composition applied to the keratinous fibers ranges, for example, from 3 to 12, or from 5 to 11. The pH can be adjusted to the desired value using acidifying or basifying agents commonly used in dyeing keratinous fibers and defined above.

The color can be developed at acidic, neutral, or alkaline pH and the at least one oxidizing agent can be added to the composition of the present disclosure at the time of use or it can be employed from an oxidizing composition comprising it, applied simultaneously or sequentially with the mixture of compositions of the present disclosure.

In at least one embodiment, this coloring is developed at neutral pH.

The ready-for-use composition which is finally applied to the keratinous fibers can be provided in various forms, such as liquids, creams, and gels or in any form appropriate for carrying out dyeing of keratinous fibers such as human hair.

Further disclosed herein is a dyeing kit or multi-compartment device comprising at least one first compartment containing a dyeing composition (A) comprising at least one coupler chosen from 6-chloro-2-methyl-5-aminophenol and salts thereof and also comprising at least one oxidation base chosen from diamino-N,N-dihydropyrazolone derivatives of formula (I) and salts thereof, such as 2,3-diamino-6,7-dihydro-1H,5H-pyrazolo[1,2-a]pyrazol-1-one, at least one second compartment containing a composition (B) chosen from fundamental and golden fundamental compositions, and at least one third compartment containing at least one oxidizing agent or an oxidizing composition comprising at least one oxidizing agent.

This device can be equipped with an applicator that makes it possible to deliver the desired mixture to the hair, such as the devices described in French Patent No. 2 586 913.

In at least one embodiment, in the dyeing kit defined above, the at least one first compartment comprises a dyeing composition (A) of coppery shade, the at least one second compartment comprises a composition (B) of fundamental shade, and the at least one third compartment comprises at least one oxidizing agent.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

COLORING PROCESS EXAMPLE

The following compositions (A)-(C) were prepared by combining the ingredients listed below. All amounts are given on a weight percentage basis, unless otherwise indicated.

Composition (A) of the "Coppery" Shade:

| | |
|---|---|
| Natural lauric acid | 2 |
| Oxyethylenated (3 EO) decyl alcohol | 12 |
| Oxyethylenated (12 EO) lauryl alcohol | 6 |
| Cetearyl alcohol ($C_{16}$-$C_{18}$, 50/50) | 10 |
| Oxyethylenated (30 EO) oleocetyl alcohol | 3.5 |
| Pyrogenic silica with a hydrophobic nature | 1 |
| Pure monoethanolamine | 1.2 |
| Polyquaternium-6 | 5 |
| Propylene glycol | 7 |
| Hexadimethrine chloride | 3 |
| Crosslinked polyacrylic acid | 0.6 |
| Diethylenetriaminepentaacetic acid, pentasodium salt, as a 40% aqueous solution | 2 |
| Ammonium thiolactate, as a 58% aqueous solution (50% as thiolactic acid) | 0.8 |
| Sodium metabisulphite | 0.71 |
| Ascorbic acid | 0.25 |
| para-Aminophenol | 0.1 |
| 6-Chloro-2-methyl-5-aminophenol | 0.8 |
| 2,3-Diamino-6,7-dihydro-1H,5H-pyrazolo[1,2-a]pyrazol-1-one dimethanesulphonate | 1.9 |
| 1-Methyl-2-hydroxy-4-aminobenzene | 0.2 |
| Aqueous ammonia (comprising 20.5% of ammonia) | 12 |
| Fragrance | 0.5 |
| Deionized water (q.s.) | q.s. for 100 |

Composition (B) of the "Golden" Shade:

| | |
|---|---|
| Natural lauric acid | 2 |
| Oxyethylenated (3 EO) decyl alcohol | 12 |
| Oxyethylenated (12 EO) lauryl alcohol | 6 |
| Cetearyl alcohol ($C_{16}$-$C_{18}$, 50/50) | 10 |
| Oxyethylenated (30 EO) oleocetyl alcohol | 3.5 |
| Pyrogenic silica with a hydrophobic nature | 1 |
| Pure monoethanolamine | 1.2 |
| Polyquaternium-6 | 5 |
| Propylene glycol | 7 |
| Hexadimethrine chloride | 3 |
| Crosslinked polyacrylic acid | 0.6 |
| Diethylenetriaminepentaacetic acid, pentasodium salt, as a 40% aqueous solution | 2 |
| Ammonium thiolactate, as a 58% aqueous solution (50% as thiolactic acid) | 0.8 |
| Sodium metabisulphite | 0.71 |
| Ascorbic acid | 0.25 |
| 1-Methyl-2,5-diaminobenzene | 0.33 |
| para-Aminophenol | 0.55 |
| Resorcinol | 0.64 |
| meta-Aminophenol | 0.07 |
| 6-Hydroxyindole | 0.055 |
| Aqueous ammonia (comprising 20.5% of ammonia) | 12 |
| Fragrance | 0.5 |
| Deionized water (q.s.) | q.s. for 100 |

Comparative Composition (C) of the "coppery" shade, the oxidation-base of which derived from diamino-N,N-dihydropyrazolone has been replaced by para-aminophenol, and comprising the specific coupler 6-chloro-2-methyl-5-aminophenol

| | |
|---|---|
| Natural lauric acid | 2 |
| Oxyethylenated (3 EO) decyl alcohol | 12 |
| Oxyethylenated (12 EO) lauryl alcohol | 6 |
| Cetearyl alcohol ($C_{16}$-$C_{18}$, 50/50) | 10 |
| Oxyethylenated (30 EO) oleocetyl alcohol | 3.5 |
| Pyrogenic silica with a hydrophobic nature | 1 |
| Pure monoethanolamine | 1.2 |
| Polyquaternium-6 | 5 |
| Propylene glycol | 7 |
| Hexadimethrine chloride | 3 |
| Crosslinked polyacrylic acid | 0.6 |
| Diethylenetriaminepentaacetic acid, pentasodium salt, as a 40% aqueous solution | 2 |
| Ammonium thiolactate, as a 58% aqueous solution (50% as thiolactic acid) | 0.8 |
| Sodium metabisulphite | 0.71 |

23
-continued

| | |
|---|---|
| Ascorbic acid | 0.25 |
| para-Aminophenol | 0.6 |
| Resorcinol | 0.01 |
| 6-Chloro-2-methyl-5-aminophenol | 1.4 |
| 6-Hydroxyindole | 0.05 |
| Aqueous ammonia (comprising 20.5% of ammonia) | 12 |
| Fragrance | 0.5 |
| Deionized water (q.s.) | q.s. for 100 |

Method of Application and Results

At the time of use, the compositions (A) and (C) were mixed with the composition (B) in a ratio by weight of 1/1 and then the resulting mixtures were mixed with an oxidizing agent in a proportion by weight of 1/1.5 (1+1.5). The oxidizing agent was an oxidizing agent of 25-volume (25 V) hydrogen peroxide type. A pH of approximately 10 was obtained.

The mixtures (A)/(B) and (C)/(B) were applied to locks of grey hair comprising 90% of natural white hairs (NW) in a proportion of 30 g of mixture per 2 g of hair. After leaving for 20 minutes at ambient temperature, the locks were rinsed, washed with a standard shampoo, rinsed again, and then dried.

Table of results

| | Color of the 90% NW keratinous fibers | H Level of tone | Highlights of the 90% NW keratinous fibers | $(R_1)(R_2)$ |
|---|---|---|---|---|
| Composition (A) + oxidizing agent* | Coppery blond | 7 | Coppery | 4 |
| Composition (B) + oxidizing agent* | Golden blond | 7 | Golden | 3 |
| Comparative Composition (C) + oxidizing agent* | Coppery blond | 7 | Coppery | 4 |
| Mixture (A)/(B) + oxidizing agent* | Golden coppery blond | 7 | Coppery | 43 |
| Comparative Mixture (C)/(B) + oxidizing agent* | Purplish blond | 7 | Golden iridescent | 23 |

Oxidizing agent*: 25-volume hydrogen peroxide

Thus, the mixture of the compositions (A)/(B) colored the keratinous fibers in a predictable way with a coppery shade which completely covered the white hairs.

On the other hand, the comparative mixture of the compositions (C)/(B) colored the fibers blond with undesirable "purplish" shades.

It is thus apparent that the presence of the oxidation base of diamino-N,N-dihydropyrazolone type of formula (I), such as the salt of 2,3-diamino-6,7-dihydro-1H,5H-pyrazolo[1,2-a] pyrazol-1-one, in the composition (A) makes it possible to prevent an unpredictable color and/or shade originating from the mixture of "fundamental" or "golden fundamental" with a "shaded" dyeing composition comprising a meta-aminophenol coupler substituted by halogen, including, for example, 6-chloro-2-methyl-5-aminophenol.

What is claimed is:

1. A process for coloring keratinous fibers comprising applying, to the fibers, a mixture of a composition (A) and of a composition (B) chosen from fundamental and/or golden fundamental and/or golden dyeing compositions;
    wherein the composition (A) comprises at least one coupler chosen from 6-chloro-2-methyl-5-aminophenol and salts thereof and at least one oxidation base chosen from 2,3-diamino-6,7-dihydro-1H,5H-pyrazolo[1,2-a] pyrazol-1-one and salts thereof
    in the presence of at least one oxidizing agent;
    wherein said composition (B), in the presence of an oxidizing agent, results, at ambient temperature on a lock of unpermed grey hair comprising 90% of white hairs, in the following values in the L*a*b* colorimetric system: a* is in the range [0;+20], b is in the range [0;+20, ] and L* is in the range [0;+50]; and
    wherein the ratio by weight of the mixture of the composition (A) to the composition (B), (A)/(B), ranges from 5/1 to 1/5.

2. The coloring process of claim 1, wherein the at least one coupler chosen from 6-chloro-2-methyl-5-aminophenol and salts thereof is present in composition (A) in an amount ranging from 0.001 to 8% by weight relative to the total weight of composition (A).

3. The coloring process of claim 1, wherein the at least one oxidation base is present in composition (A) in an amount ranging from 0.001% to 8% by weight relative to the total weight of composition (A).

4. The coloring process of claim 1, wherein the composition (B) comprises at least one oxidation base chosen from para-phenylenediamines and salts thereof.

5. The coloring process of claim 4, wherein the para-phenylenediamines and salts thereof are chosen from para-toluenediamine, para-phenylenediamine, and salts thereof.

6. The coloring process of claim 4, wherein the at least one oxidation base is present in composition (B) in an amount of less than or equal to 5 mmol per 100 g of composition (B).

7. The coloring process of claim 1, wherein composition (B) further comprises at least one coupler chosen from meta-diphenols, meta-aminophenols, and meta-phenylenediamines.

8. A multi-compartment device comprising at least one first compartment containing a dyeing composition (A) comprising at least one coupler chosen from 6-chloro-2-methyl-5-aminophenol and salts thereof and at least one oxidation base chosen from 2,3-diamino-6,7-dihydro-1H,5H-pyrazolo[1,2-a]pyrazol-1-one and salts thereof;
    at least one second compartment containing a composition (B) chosen from fundamental and/or golden fundamental and/or golden compositions wherein said composition (B) in the presence of an oxidizing agent, it results, at ambient temperature on a lock of unpermed grey hair comprising 90% of white hairs, in the following values in the L*a*b* colorimetric system: a* is in the range [0;+20, ], b is in the range [0;+20] and L* is in the range [0;+50], and
    at least one third compartment containing at least one oxidizing agent or an oxidizing composition comprising at least one oxidizing agent;
    wherein composition (A) and composition (B) are present in a ratio by weight (A)/(B) ranging from 5/1 to 1/5.

* * * * *

UNITED STATES PATENT AND TRADEMARK OFFICE
CERTIFICATE OF CORRECTION

PATENT NO. : 7,918,900 B2
APPLICATION NO. : 11/812616
DATED : April 5, 2011
INVENTOR(S) : Cottard et al.

Page 1 of 1

It is certified that error appears in the above-identified patent and that said Letters Patent is hereby corrected as shown below:

In claim 1, col. 24, line 16, "[0;+20, ]" should read --[0;+20],--.

In claim 8, col. 24, line 51, "compositions wherein" should read --compositions, wherein--.

In claim 8, col. 24, line 52, "(B) in" should read --(B), in--.

In claim 8, col. 24, line 52, "agent, it results" should read --agent, results--.

In claim 8, col. 24, line 56, "[0;+20, ]," should read --[0;+20],--.

In claim 8, col. 24, line 56, "[0;+20]" should read --[0;+20],--.

Signed and Sealed this
Seventh Day of June, 2011

David J. Kappos
*Director of the United States Patent and Trademark Office*